United States Patent
Friedman et al.

(10) Patent No.: US 11,623,071 B2
(45) Date of Patent: Apr. 11, 2023

(54) GUIDE WIRE ACTIVATION MECHANISM AND PROXIMAL ACTUATION MECHANISM

(71) Applicant: RAPID MEDICAL LTD., Yokneam (IL)

(72) Inventors: Aharon Friedman, Haifa (IL); Matan Gedulter, Givat Ela (IL); Moshe Miller, Jerusalem (IL); Ronen Eckhouse, Shimshit (IL)

(73) Assignee: RAPID MEDICAL LTD., Yokneam (IL)

( * ) Notice: Subject to any disclaimer, the term of this patent is extended or adjusted under 35 U.S.C. 154(b) by 238 days.

(21) Appl. No.: 16/772,111

(22) PCT Filed: Dec. 12, 2018

(86) PCT No.: PCT/IB2018/001571
§ 371 (c)(1),
(2) Date: Jun. 11, 2020

(87) PCT Pub. No.: WO2019/116102
PCT Pub. Date: Jun. 20, 2019

(65) Prior Publication Data
US 2021/0085928 A1   Mar. 25, 2021

Related U.S. Application Data

(60) Provisional application No. 62/597,888, filed on Dec. 12, 2017.

(51) Int. Cl.
*A61M 25/09* (2006.01)
*A61M 25/01* (2006.01)

(52) U.S. Cl.
CPC ......... *A61M 25/09* (2013.01); *A61M 25/0147* (2013.01); *A61M 25/0169* (2013.01);
(Continued)

(58) Field of Classification Search
CPC .............. A61M 25/09; A61M 25/0147; A61M 25/0169; A61M 2025/09075;
(Continued)

(56) References Cited

U.S. PATENT DOCUMENTS

| 4,827,941 A | 5/1989 | Taylor et al. |
| 4,940,062 A | 7/1990 | Hampton et al. |

(Continued)

FOREIGN PATENT DOCUMENTS

| EP | 0410557 A2 | 1/1991 |
| JP | H 02-04390 A | 1/1990 |

(Continued)

OTHER PUBLICATIONS

Extended European Search Report from the European Patent Office for counterpart European Application No. 18888733.5, dated Sep. 22, 2021 (5 pages).

(Continued)

*Primary Examiner* — Sean P Dougherty
(74) *Attorney, Agent, or Firm* — Finnegan, Henderson, Farabow, Garrett & Dunner, LLP (57) ABSTRACT

An intraluminal guide wire may include an elongated shaft extending between a distal and a proximal end. The guide wire may include a user actuation segment positioned proximal to the proximal end of the shaft and configured for movement relative to the shaft. The guide wire may include a core wire affixed to the user actuation segment and the distal end of the shaft. The guide wire may also include an inner member having a proximal end situated at least partially within and fixed relative to the user actuation segment and a distal end situated partially within the shaft, the core wire passing through the inner member. The guide wire may be configured with a distal segment of the inner member within the shaft exhibiting a friction-based restraint (Continued)

on movement within the shaft. The friction-based restraint on movement may be a frictional force between the inner member and the shaft.

14 Claims, 9 Drawing Sheets

(52) U.S. Cl.
CPC ............. *A61M 2025/09075* (2013.01); *A61M 2025/09116* (2013.01); *A61M 2025/09125* (2013.01)

(58) Field of Classification Search
CPC ......... A61M 2025/09116; A61M 2025/09125; A61M 25/09041; A61M 25/09025
See application file for complete search history.

(56) References Cited

U.S. PATENT DOCUMENTS

| | | | |
|---|---|---|---|
| 5,497,782 A * | 3/1996 | Fugoso | A61M 25/0169 600/585 |
| 2003/0181827 A1 | 9/2003 | Hojeibane et al. | |
| 2005/0070844 A1 * | 3/2005 | Chow | A61M 25/0013 604/95.04 |
| 2006/0200047 A1 | 9/2006 | Galdonik et al. | |
| 2008/0140101 A1 | 6/2008 | Carley et al. | |
| 2010/0004722 A1 | 1/2010 | Taubert et al. | |
| 2010/0305475 A1 | 12/2010 | Hinchliffe et al. | |
| 2011/0071435 A1 | 3/2011 | Shamay et al. | |
| 2014/0343457 A1 | 11/2014 | Shekalim et al. | |
| 2014/0350568 A1 | 11/2014 | Shekalim et al. | |
| 2015/0265806 A1 * | 9/2015 | Kawaguchi | A61M 25/0028 604/539 |
| 2017/0209871 A1 | 7/2017 | Ring | |
| 2017/0259041 A1 * | 9/2017 | Lenker | A61M 25/09041 |

FOREIGN PATENT DOCUMENTS

| | | |
|---|---|---|
| JP | H 02-63476 A | 3/1990 |
| JP | 2002-516729 A | 6/2002 |

OTHER PUBLICATIONS

First Office Action and Search Report from China National Intellectual Property Administration for corresponding Chinese Application No. 201880079987.7, dated Dec. 10, 2021, with Translation (20 pages).
International Search Report for International Application No. PCT/IB2018/001571, dated May 31, 2019 (3 pages).
Written Opinion of the International Searching Authority for International Application No. PCT/IB2018/001571, dated May 31, 2019 (7 pages).
Office Action in corresponding Japanese Application No. 2020-531926, dated Oct. 19, 2022, with Translation (7 pages).

* cited by examiner

GUIDE WIRE ACTIVATION MECHANISM AND PROXIMAL ACTUATION MECHANISM

CROSS-REFERENCE TO RELATED APPLICATION

This application is a U.S. national stage entry under 35 U.S.C. § 371 of International Application No. PC/IB2018/001571 filed Dec. 12, 2018, which claims the benefit of priority from U.S. Provisional Application No. 62/597,888, filed Dec. 12, 2017, both of which are herein incorporated by reference in their entireties.

TECHNICAL FIELD

This disclosure relates to intravascular and/or intraluminal medical devices. Various embodiments of the present disclosure relate to deflectable guide wires for introduction of catheters and other medical devices into a body cavity.

BACKGROUND

Guide wires may be used to advance intravascular and intraluminal medical devices, such as catheters and blood clot removal devices, to treatment sites within the body. In some instances, the guide wire may be passed through the body until the distal tip of the guide wire is situated at the desired treatment site. After placement of the guide wire, the intraluminal device may be advanced over the guide wire and used to treat medical conditions at the treatment site.

To pass through tortuous anatomy, the guide wire may include a steering mechanism such as a pull wire, which may be configured to bend or deflect the distal tip of the guide wire in a desired direction. The pull wire may be secured to a user actuation segment, such as a handle at the proximal end of the guide wire, which may be moved axially by the user relative to the guide wire to control deflection and straightening of the distal tip of the guide wire. Because the user actuation segment is configured for axial movement relative to the guide wire, it may be difficult to prevent movement of the user actuation segment during operations involving use of the guide wire, such as when the guide wire is rotated or when an intraluminal device is advanced over the guide wire. As a result, the distal tip of the guide wire may be inadvertently bent or straightened, causing the guide wire to be diverted from the desired delivery route and making it difficult to pass the guide wire through the anatomy.

Thus, there remains a need for intraluminal guide wires having a locking mechanism configured to secure the user actuation segment to avoid inadvertent movement relative to the guide wire, but which does not hinder bending and straightening of the distal tip of the guide wire with the user actuation segment. Embodiments of the present disclosure provide a self-locking feature for a guide wire that may be configured to securely hold the user actuation segment and the guide wire in their respective positions until the user actuation segment is repositioned by the user.

SUMMARY

Embodiments of the present disclosure include an intraluminal guide wire that includes a hollow elongated shaft extending between a distal end thereof and a proximal end thereof. Consistent with an embodiment, the intraluminal guide wire may include a user actuation segment positioned proximal to the proximal end of the hollow elongated shaft, the user actuation segment configured for movement relative to the hollow elongated shaft. The intraluminal guide wire may include a core wire extending between the user actuation segment and a distal portion of the hollow elongated shaft. The intraluminal guide wire may also include an inner member. The inner member may have a proximal end thereof positioned at least partially within and fixed relative to the user actuation segment. The inner member may additionally have a distal end thereof configured for placement at least partially within and for axial movement relative to the hollow elongated shaft, the core wire passing through the inner member. In some embodiments, the intraluminal guide wire may be configured such that a locking segment of the inner member configured for placement within the hollow elongated shaft is configured to exhibit a friction-based restraint on movement within the hollow elongated shaft, the friction-based restraint on movement being a frictional force between an outer surface of the inner member and an inner surface of the hollow elongated shaft.

In some embodiments, the intraluminal guide wire may include a deflectable segment situated at least partially within the distal portion of the hollow elongated shaft. The core wire may be affixed to the deflectable segment. The core wire may be configured such that movement of the user actuation segment causes deflection of the deflectable segment.

In some embodiments, the locking segment of the inner member may also include at least one bend, such that when the locking segment of the inner member is inserted within the hollow elongated shaft, the at least one bend of the inner member may exert the frictional force upon the inner surface of the hollow elongated shaft.

In some embodiments, the locking segment of the inner member may be sufficiently flexible such that the at least one bend may be configured to be partially straightened when the locking segment of the inner member is inserted within the hollow elongated shaft.

In some embodiments, the locking segment of the inner member may include a plurality of bends. Each bend of the plurality of bends may be configured to exert the frictional force upon separate portions of the inner surface of the hollow elongated shaft.

In some embodiments, the intraluminal device may include a connection member fixed relative to the user actuation segment and extending from the proximal end of the user actuation segment. The connection member may include at least one bend, such that the at least one bend of the connection member may be configured to exert a second frictional force upon an inner surface of a second hollow elongated shaft.

In some embodiments, an outer diameter of the user actuation segment may be smaller than or substantially equal to an outer diameter of the hollow elongated shaft.

In some embodiments, the intraluminal device may include an outer handle fixed relative to the user actuation segment. The outer handle may be configured to receive the proximal end of the hollow elongated shaft therein.

In some embodiments, at least a portion of the core wire may extend within and may be secured relative to the outer handle.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

BRIEF DESCRIPTION OF THE DRAWINGS

The accompanying drawings, which are incorporated in and constitute a part of this specification, illustrate disclosed embodiments and, together with the description, serve to explain the disclosed embodiments.

Annotations appearing in the figures are exemplary only, and are not restrictive of the invention as claimed.

DETAILED DESCRIPTION

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

Embodiments of the present disclosure relate generally to medical guide wires and methods for using guide wires to deliver medical devices into body cavities. More particularly, embodiments of the present disclosure relate to guide wires having a user actuation segment configured to control bending and/or deflection of the distal end of the guide wire. Exemplary guide wires may include a self-locking feature configured to secure the user actuation segment to avoid movement relative to the guide wire, so as to hold the distal end of the guide wire in a desired configuration, e.g., during delivery of a medical device over the guide wire to a body cavity.

Figure 1A:
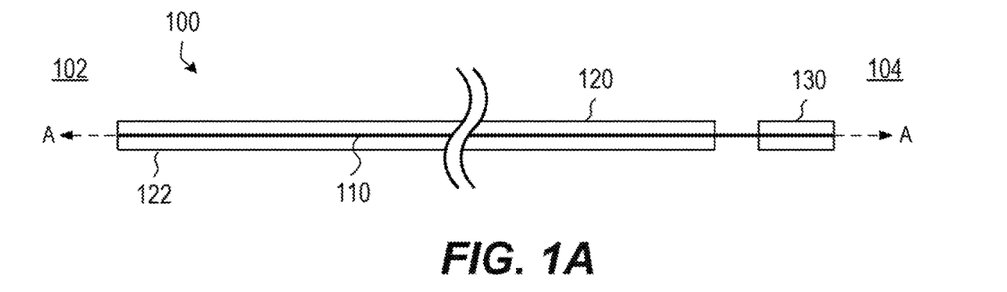
FIG. 1A is an illustration of an exemplary guide wire in a first configuration, consistent with various embodiments of the present disclosure.
Figure 1B:
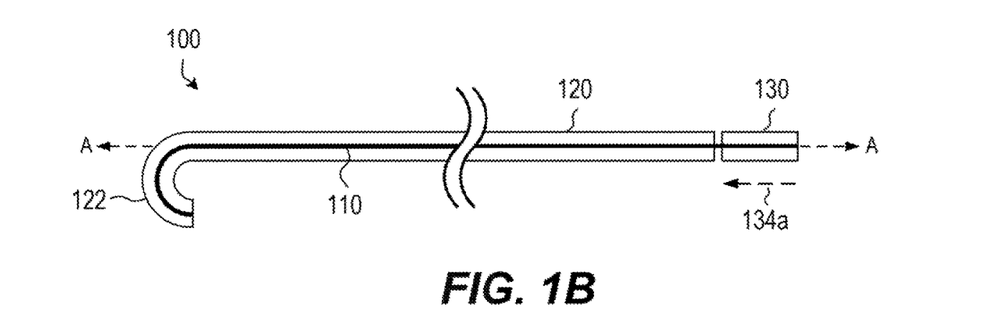
FIG. 1B is an illustration of the guide wire of FIG. 1A in a second configuration, consistent with various embodiments of the present disclosure.
Figure 1C:
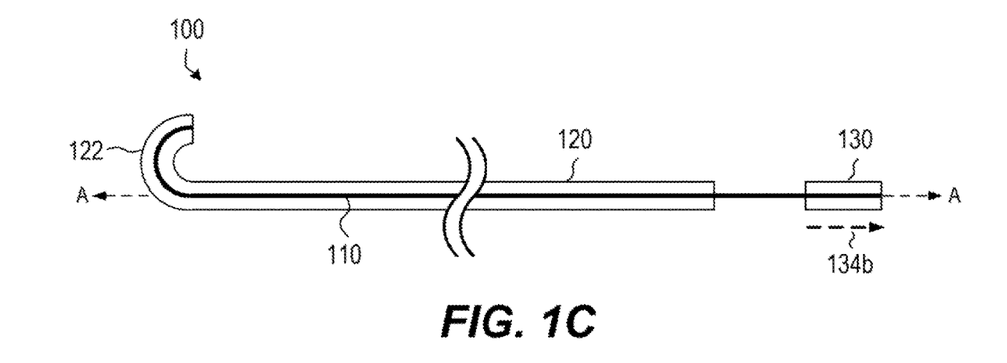
FIG. 1C is an illustration of the guide wire of FIG. 1A in a third configuration, consistent with various embodiments of the present disclosure.

As illustrated in FIGS. 1A-1C, a guide wire 100 consistent with the present disclosure may include a hollow outer shaft 120 extending along a longitudinal axis A between a distal end 102 of the guide wire and a proximal end 104 of the guide wire. In the present disclosure, the term "proximal" refers to the end of a device (e.g., guide wire 100) that is closer to the device operator during use, and the term "distal" refers to the end of a device that is further from the device operator during use. Outer shaft 120 may be constructed of a biocompatible material, such as stainless steel, nitinol, PEEK, urethane, and/or polycarbonate. Guide wire 100 may have any appropriate length, for example between approximately 100 centimeters and approximately 350 centimeters, such that the guide wire is at least long enough to extend from a location outside of a patient's body to a desired site within the body.

Outer shaft 120 may include a deflectable segment 122 on its distal end. Deflectable segment 122 may be configured for greater flexibility than outer shaft 120, such that deflectable segment 122 may curve or deflect laterally in one or more directions while outer shaft 120 remains straightened along longitudinal axis A. In some embodiments, deflectable segment 122 may include a helically coiled wire constructed of an elastic material, such as stainless steel, nickel alloy, nickel-titanium alloy (e.g., Nitinol), platinum, tantalum, or titanium. The helical coil of deflectable segment 122 may extend parallel to longitudinal axis A and may be connected to outer shaft 120, such as by solder, welding, adhesive, one or more mechanical fasteners, or other suitable means. In some alternative embodiments, deflectable segment 122 may constitute an extension or portion of outer shaft 120, fabricated or treated to render deflectable segment 122 more flexible than outer shaft 120. For example, deflectable segment 122 may include a series of cuts or grooves along one side, allowing deflectable segment 122 to bend or deflect in the direction faced by the side of the segment 122 having the cuts or grooves. In some embodiments, the outer diameter of the deflectable segment 122 may be substantially equal to the outer diameter of the outer shaft 120. Alternatively, the outer diameter of the deflectable segment 122 may be larger than or smaller than the outer diameter of the outer shaft 120. In some embodiments, deflectable segment 122 may include a rounded, blunt distal tip.

In some embodiments, deflectable segment 122 may have an axial length of between approximately 0.5 cm and approximately 10.0 cm. For example, deflectable segment 122 may have an axial length of between approximately 1.0 cm and approximately 5.0 cm. In various embodiments, and without limitation, the deflectable segment 122 may have an axial length that is at least one of: 0.5 cm, 1.0 cm, 1.5 cm, 2.0 cm, 2.5 cm, 3.0 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 9.5 cm, 10.0 cm, or a range thereof.

Guide wire 100 may include a user actuation segment 130 at its proximal end 104. User actuation segment 130 may include a member configured as a handle, which may be movable relative to outer shaft 120. In some embodiments, at least a portion of user actuation segment 130 may be hollow and may have an outer diameter substantially equal to the outer diameter of outer shaft 120. Guide wire 100 may include a core wire 110, which may connect to deflectable segment 122 and extend through the inner lumen of outer shaft 120 to the proximal end of outer shaft 120, and which may be connected to the user actuation segment 130.

Due to the connection between user actuation segment 130 and core wire 110, axial movement of user actuation segment 130 may cause corresponding axial movement of core wire 110 relative to the outer shaft 120. In some embodiments, axial motion of the user actuation segment 130 relative to the outer shaft 120 (shown in FIGS. 1B and 1C by dotted arrows 134a and 134b) may cause deflection and/or straightening of the deflectable segment 122 relative to the remainder of outer shaft 120. In the example illustrated in FIGS. 1A-C, deflectable segment 130 may be configured to remain in a substantially straightened configuration (FIG. 1A) in the absence of an applied axial force from core wire 110. In some embodiments, proximal movement of the user actuation segment 130 (represented by arrow 134b in FIG. 1C) may pull core wire 110 in the proximal direction, causing the deflectable segment 122 to deflect or curve in a first direction away from longitudinal axis A (FIG. 1C). Additionally, or alternatively, distal movement of the user actuation segment 130 (represented by arrow 134a in FIG. 1B) may push core wire 110 in the distal direction, causing the deflectable segment 122 to deflect or curve in a second direction away from longitudinal axis A that is opposite to the first direction (FIG. 1B). The curvature of deflectable segment 122 away from longitudinal axis A may be provided, at least in part, by the flexibility of deflectable segment 122.

In alternative embodiments, deflectable segment 122 may be configured to remain in a deflected or curved configuration (such as the configurations illustrated in FIG. 1B or 1C) in the absence of an applied axial force from core wire 110. Axial movement of user actuation segment 130 (and, thus, core wire 110) may cause straightening of deflectable segment 122.

The core wire 110 may be constructed of one or more materials having sufficient strength to push and pull the deflectable segment 122 so as to control the curvature of the deflectable segment, while still being sufficiently flexible to bend and curve within the deflectable segment. For example, the corewire 110 may be constructed of stainless steel alloys, nickel titanium alloys, or polymers. Core wire 110 may be connected to deflectable segment 122 and to user actuation segment 130 by solder, welding, adhesive, one or more mechanical fasteners, or other suitable means. In some embodiments, core wire 110 may be connected to the distal tip of deflectable segment 122. Additionally, or alternatively, core wire 110 may be connected to another portion of deflectable segment 122.

In some embodiments, some or all of the guide wire 100 may include an outer coating, such as PTFE, ePTFE, FEP, polyester, or polyurethane, to enhance biocompatibility of guide wire 100 and to smooth the outer surface(s) of the guide wire. For example, outer shaft 120, deflectable segment 122, and optionally, user actuation segment 130 may be so treated with an outer coating. Additionally, or alternatively, core wire 110 may be coated with a material such as PTFE, ePTFE, FEP, polyester, or polyurethane, to enhance the ability of the core wire 110 to slide within outer shaft 120.

Figure 2:
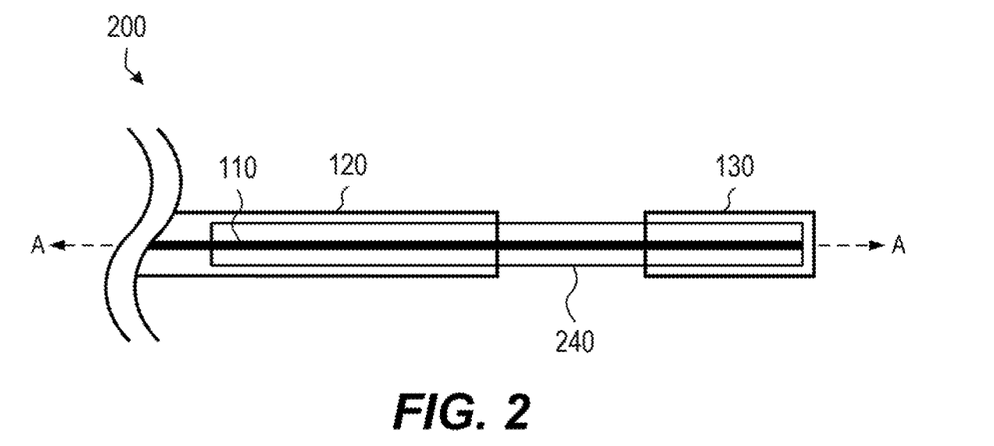
FIG. 2 is an illustration of another exemplary guide wire, consistent with various embodiments of the present disclosure.

FIG. 2 illustrates the proximal end of another exemplary guide wire 200. Guide wire 200 may include an inner member 240, which may be situated at least partially within outer shaft 120 and user actuation segment 130, with core wire 110 extending through the inner member 240. Inner member 240 may be connected to the user actuation segment 130 or to the outer shaft 120 in order to guide and support the axial movement of the user actuation segment 130 relative to the outer shaft 120.

Figure 3:
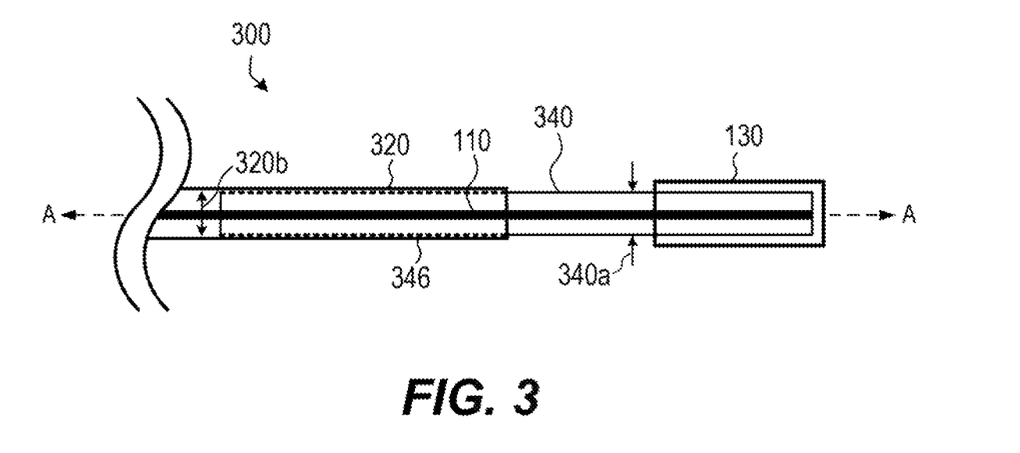
FIG. 3 is an illustration of a further exemplary guide wire, consistent with various embodiments of the present disclosure.

FIG. 3 illustrates the proximal end of a further exemplary guide wire 300. Guide wire 300 may include an inner member 340 situated at least partially within outer shaft 320 and user actuation segment 130. In some embodiments, inner member 340 may be connected to user actuation segment 130 by solder, welding, adhesive, one or more mechanical fasteners, or other suitable means. Inner member 340 may be configured for axial movement relative to outer shaft 320. In some embodiments, a portion of inner member 340 (such as portion 346) may be configured to exhibit intended friction with outer shaft 320. This is depicted in FIG. 3, generally, by illustrating the outer portion 346 of inner member 340 with the use of a dashed line. The friction between inner member 340 and outer shaft 320 may form a self-locking feature, such that inner member 340 may move axially relative to the outer shaft 320 when the user exerts sufficient axial force on user actuation member 130 so as to overcome the friction. However, in the absence of a user-applied axial force, the friction may hold inner member 340 and outer shaft 320 in their relative axial positions until the user applies an axial force to user actuation member 130.

Consistent with embodiments of the present disclosure, the intended friction may be designed and implemented in a number of ways. In some embodiments, the intended friction may be implemented through the use of interference tolerances between the inner member and the outer shaft. For example, inner member 340 may have an outer diameter 340a of between approximately 0.2 mm and approximately 3.0 mm, while the outer shaft 320 may have an inner diameter 320b configured to have interference fit tolerance with relation to outer diameter 340a, such that friction is formed between the outer diameter of inner member 340 and the inner diameter of outer shaft 320.

Figure 4A:
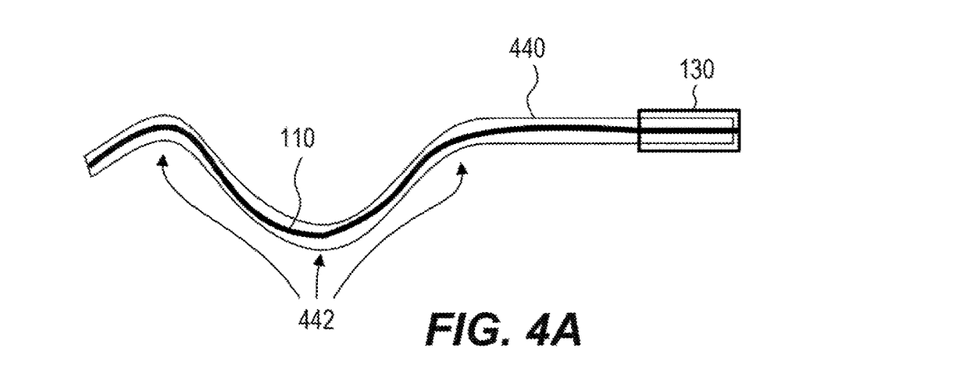
FIG. 4A is an illustration of an exemplary inner member of a guide wire, consistent with various embodiments of the present disclosure.

In some alternative embodiments, the inner member may be shaped or otherwise configured to contact the inner lumen of the outer shaft, thus creating friction between them. For example, as illustrated in FIG. 4A, the inner member 440 may exhibit a geometry with one or more designed bends 442 when the inner member is situated outside of the outer shaft 420. In some embodiments, the inner member 440 may be configured to assume a serpentine configuration, such that the inner member may include one or more designed bends 442 separated by substantially straight sections. Inner member 440 may include one bend, two bends, three bends, four bends, five bends, six bends, or any other suitable number of bends. In other embodiments, inner member 440 may include a different bending pattern, such as a zigzag pattern, a sinusoidal pattern, or a helical coil pattern. In some embodiments, the inner member 440 may include a combination of different bending patterns, for example, a serpentine portion and a sinusoidal portion.

Figure 4B:
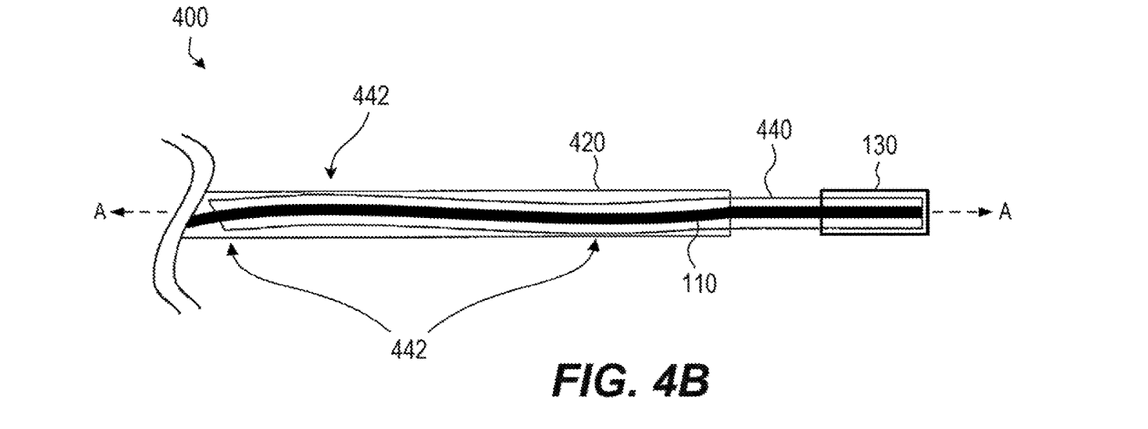
FIG. 4B is an illustration of an exemplary guide wire including the inner member of FIG. 4A, consistent with various embodiments of the present disclosure.

Inner member 440 may be constructed of any suitable flexible material known to those skilled in the art. Suitable flexible materials can include, but are not limited to, polymers, metals, metal alloys, and combinations thereof. In some embodiments, for example, inner member 440 may be constructed from superelastic metals such as Nitinol. As a result, the inner member 440 may act as a loaded spring once the inner member is straightened inside outer shaft 420 to ensure continuous and constant friction between inner member 440 and the outer shaft 420 at designated pressure/friction points 442. For example, guide wire 400 illustrated in FIG. 4B may include an inner member 440 configured to be sufficiently straightened for placement within the outer shaft 420. However, due to the spring-like configuration of the inner member 440, the inner member may bend within the outer shaft 420 until the bends 442 contact the inner surface of the outer shaft. This may create friction between the inner member 440 and the outer shaft 420 at least at the locations of the bends 442. When the user exerts sufficient axial force on the user actuation segment 130 to overcome this friction, inner member 440 may be moved axially relative to outer shaft 420, allowing bending or straightening of the deflectable segment (not shown in FIG. 4B). In the absence of a user-exerted force, the intended friction may hold inner member 440 and outer shaft 420 in their respective axial positions. Advantageously, this friction may prevent inadvertent movement or dislodging of the inner member and outer shaft, allowing the deflectable segment to remain in its intended bent or straightened configuration. For example, during maneuvering or rotation of the guide wire 400, or while a medical device is delivered over guide wire 400, inner member 440 and outer shaft 420 may be held together by the friction, preventing the deflectable segment from being inadvertently bent or straightened. As illustrated in FIGS. 4A and 4B, core wire 110 may be sufficiently flexible so as to bend within the curvature of the inner member 440.

In alternative embodiments, the inner member may be connected to the outer shaft, such as by solder, welding, adhesive, one or more mechanical fasteners, or other suitable means. In such embodiments, the inner member may be configured for axial movement relative to the user actuation segment, with intended friction formed between the inner member and the user actuation segment by the exemplary mechanisms discussed above.

Figure 5:
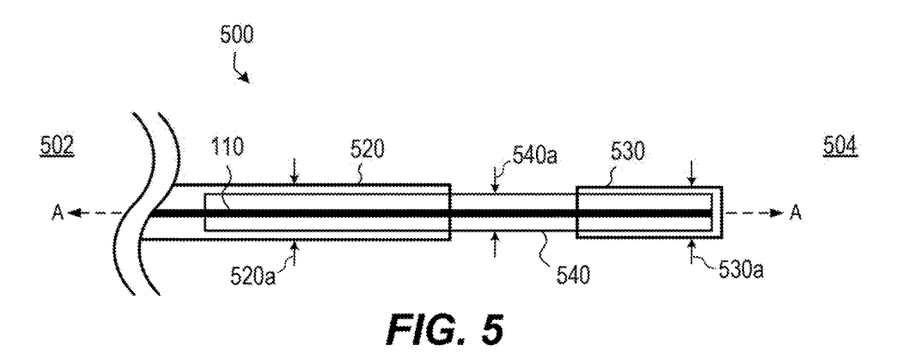
FIG. 5 is an illustration of a still further exemplary guide wire, consistent with various embodiments of the present disclosure.

FIG. 5 illustrates another exemplary guide wire 500. In some embodiments, the outer diameter 530a of the user actuation segment 530 may be substantially equal to the outer diameter 520a of the outer shaft 520. Alternatively, the outer diameter 530a of the user actuation segment 530 may be smaller than the outer diameter 520a of the outer shaft 520. At least one of the user actuation segment 530 and the outer shaft 520 may have an outer diameter between 0.25 mm and 3.0 mm. For example, at least one of the user actuation segment 530 and the outer shaft 520 may have an outer diameter in a range between 0.36 mm and 0.42 mm in some embodiments. In various embodiments, and without limitation, at least one of the user actuation segment 530 and the outer shaft 520 may have an outer diameter that is at least one of: 0.25 mm, 0.26 mm, 0.27 mm, 0.28 mm, 0.29 mm, 0.30 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.55 mm, 0.60 mm, 0.65 mm, 0.70 mm, 0.75 mm, 0.80 mm, 0.85 mm, 0.90 mm, 0.95 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, or a range thereof.

In some embodiments, the outer diameter of the deflectable segment may be substantially equal to the outer diameter 520a of the outer shaft 520. In some alternative embodiments, the outer diameter of the deflectable segment may be larger than or smaller than the outer diameter 520a of the outer shaft 520. Portions of the outer shaft 520 and the user actuation segment 530 may be hollow such that the inner member 540 may be received therein. Accordingly, the inner member 540 may have an outer diameter 540a that is smaller than the inner diameters of the outer shaft 520 and the user actuation segment 530. Inner member 540 may have an outer diameter 540a of between 0.15 mm and 3.0 mm. In some embodiments, inner member 540 may have an outer diameter 540a in a range of between 0.16 mm and 0.22 mm; for example, inner member 540 may have an outer diameter 540a of 0.19 mm. In various embodiments, and without limitation, inner member 540 may have an outer diameter 540a that is at least one of: 0.15 mm, 0.16 mm, 0.17 mm, 0.18 mm, 0.19 mm, 0.20 mm, 0.21 mm, 0.22 mm, 0.23 mm, 0.24 mm, 0.25 mm, 0.26 mm, 0.27 mm, 0.28 mm, 0.29 mm, 0.30 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.55 mm, 0.60 mm, 0.65 mm, 0.70 mm, 0.75 mm, 0.80 mm, 0.85 mm, 0.90 mm, 0.95 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, or a range thereof.

In some embodiments the outer diameters of the user actuation segment 530 and the outer shaft 520 may enable back loading of the guide wire 500 into various other compatible devices That is, the outer diameters of the user actuation segment 530 and the outer shaft 520 may enable a medical device (e.g., a catheter) to be loaded onto user actuation segment 530 from the proximal end 504 and advanced distally over the user actuation segment 530 and the outer shaft 520 towards distal end 502.

Figure 6A:
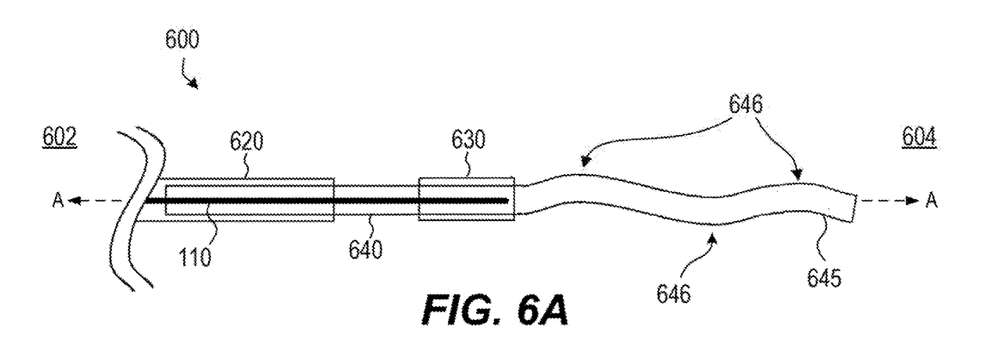
FIGS. 6A and 6B illustrate another exemplary guide wire, consistent with various embodiments of the present disclosure.
Figure 6B:
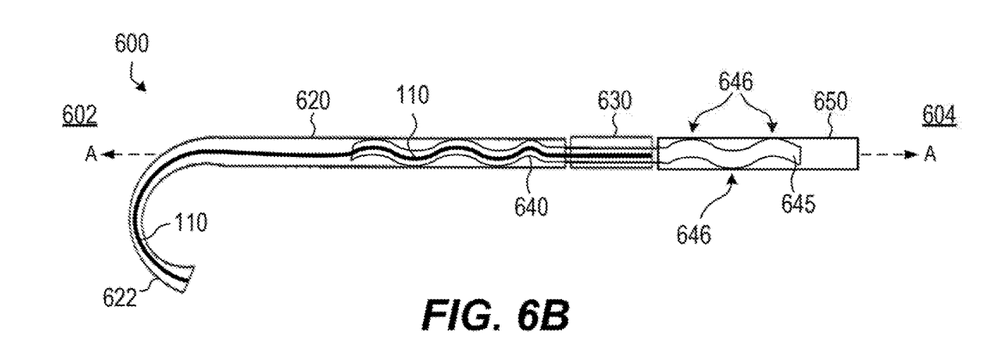

FIGS. 6A and 6B illustrate another exemplary guide wire 600 having a connection member 645 added to or extending from the proximal end of the user actuation segment 630. The guide wire 600 consistent with the present disclosure may include a hollow shaft 620 extending along a longitudinal axis A between a distal end 602 of the guide wire and a proximal end 604 of the guide wire. In some embodiments, connection member 645 may be integrally formed with inner member 640, such that the connection member constitutes an extension of the inner member 640. In some alternative embodiments, the connection member 645 may be connected to inner member 640, such as by solder, welding, adhesive, one or more mechanical fasteners, or other suitable means. In some embodiments, connection member 645 may be directly connected to the user actuation segment 630. Alternatively, connection member 645 may be secured relative, to the user actuation segment 630 due to the connection between the user actuation segment 630 and the inner member 640. In some embodiments, connection member 645 may have an outer diameter that is substantially equal to or smaller than the outer diameter of the user actuation segment 630.

Connection member 645 may be configured to allow connection of an extension wire, docketing wire, shaft, or any other auxiliary devices (such as device 650) to the guide wire 600. For example, and as illustrated in FIG. 6B, an auxiliary device 650 may be loaded onto the connection member 645 from the proximal end 604 and advanced distally until the auxiliary device 650 is securely mounted upon the connection member 645. In some embodiments, consistent with the disclosure, a connection member 645 (for example, with an extension wire or docketing wire connected thereto) may be configured to extend proximally beyond a proximal end of a catheter positioned over the guide wire 600. Such an extension may allow a user (e.g., a physician) to manipulate and reposition the catheter without losing access to the proximal end of the guide wire and without inadvertent removal of the distal end of the guide wire from an operation location within a body.

As shown in FIGS. 6A and 6B, the connection member 645 may also incorporate a design with intended friction for a firm connection with the auxiliary device 650, similar to the aforementioned exemplary inner member. For example, as illustrated in FIG. 6A, the connection member 645 may exhibit a geometry with one or more designed bends 646 when the connection member is situated outside of the auxiliary device 650. In some embodiments, the connection member 645 may be configured to assume a serpentine configuration, such that the connection member may include one or more designed bends 646 separated by substantially straight sections. Connection member 645 may include one bend, two bends, three bends, four bends, five bends, six bends, or any other suitable number of bends. In other embodiments, connection member 645 may include a different bending pattern, such as a zigzag pattern, a sinusoidal pattern, or a helical coil pattern. In some embodiments, the connection member 645 may include a combination of different bending patterns, for example, a serpentine portion and a sinusoidal portion.

Connection member 645 may be constructed of any suitable flexible material known to those skilled in the art. Suitable flexible materials can include, but are not limited to, polymers, metals, metal alloys, and combinations thereof. In some embodiments, for example, connection member 645 may be constructed from superelastic metals such as Nitinol. As a result, the connection member 645 may be configured to be sufficiently straightened for placement within the auxiliary device 650. However, due to the spring-like configuration of the connection member 645, the connection member may bend within the auxiliary device 650 until the bends 646 contact the inner surface of the auxiliary device 650. This may create friction between the connection member 645 and the auxiliary device 650 at least at the locations of the bends 646. When the user exerts sufficient axial force on the auxiliary device 650, this friction may be overcome and the auxiliary device 650 may be distally advanced over the connection member 645. In the absence of user-exerted force, however: the friction may hold connection member 645 and the auxiliary device 650 in their respective axial positions.

In some embodiments, including the embodiment depicted in FIG. 6B, the inner member 640 and the connection member 645 may be configured to frictionally engage the outer shaft 620 and the auxiliary device 650, respectively, according to the exemplary configurations discussed above. Advantageously, this arrangement may allow the auxiliary device 650 to remain secured to the guide wire 600, while also maintaining the deflectable segment 622 in a desired straightened or bent configuration, due to the fixed relative positions of the user actuation segment 630 and the outer shaft 620. Additionally, or alternatively, the user may adjust the curvature of the deflectable segment 622 by axially moving the user actuation segment 630, which may cause corresponding axial movement of the inner member 640, the connection member 645, and the auxiliary device 650. This may allow the auxiliary device to remain secured to the guide wire 600, even during use of the user actuation segment 630 to bend or straighten the deflectable segment 622.

Figure 7:
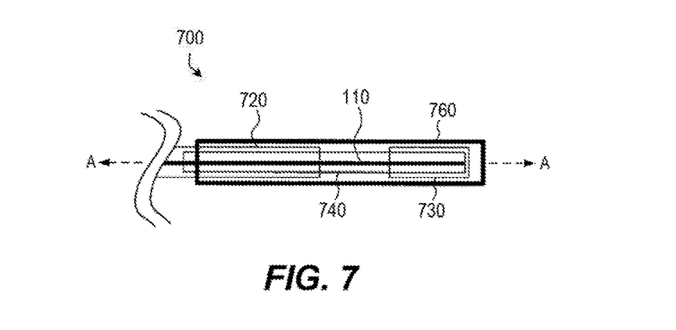
FIG. 7 is an illustration of an exemplary guide wire with an outer member, consistent with various embodiments of the present disclosure.

FIG. 7 illustrates an exemplary guide wire 700 including a user actuation segment 730 having an outer member 760 situated upon it. In some embodiments, user actuation segment 730 may be entirely received within outer member 760; alternatively, a portion of the user actuation segment 730 may extend from the outer member 760. The outer member 760 may also receive at least a portion of the outer shaft 720 therein. In some embodiments, the user actuation segment 730 and the outer member 760 may be secured together, such that the outer member 760 may be axially moved relative to the outer shaft 720 to control the curvature of the deflectable segment (not pictured). The outer member 760 may be configured as a handle and may offer improved support and usability. The outer member 760 may be permanently or removably fixed to the user actuation segment 730.

Figure 8:
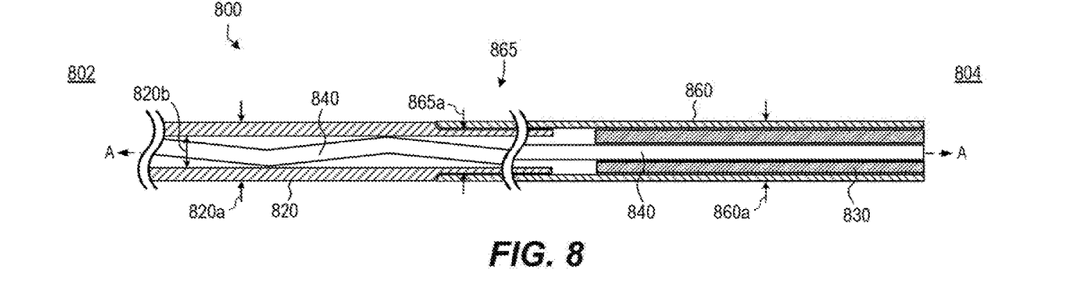
FIG. 8 is an illustration of another exemplary guide wire with an outer member, consistent with various embodiments of the present disclosure.

FIG. 8 illustrates an exemplary guide wire 800 including an outer member 860, which may be configured as a proximal end friction handle section. User actuation segment 830 may be situated within outer member 860, and may secure outer member 860 relative to inner member 840. Inner member 840 may extend from the distal end of the outer member 860. In some embodiments, the outer member 860 may have an outer diameter 860a that is substantially equal to the outer diameter 820a of outer shaft 820. Alternatively, outer diameter 860a of the outer member 860 may be larger than the outer diameter 820a of the outer shaft 820.

Outer member 860 may have an outer diameter 860a of between approximately 0.3 mm and approximately 3.0 mm. In some embodiments, outer member 860 may have an outer diameter 860a in a range of between 0.36 mm and 0.42 mm. In various embodiments, and without limitation, outer member 860 may have an outer diameter 860a that is at least one of 0.30 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.51 mm, 0.52 mm, 0.53 mm, 0.54 mm, 0.55 mm, 0.56 mm, 0.57 mm, 0.58 mm, 0.59 mm, 0.60 mm, 0.65 mm, 0.70 mm, 0.75 mm, 0.80 mm, 0.85 mm, 0.90 mm, 0.95 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, or a range thereof.

Additionally, or alternatively, the outer shaft 820 may have an outer diameter 820a of between approximately 0.25 mm and approximately 0.6 mm. In some embodiments, outer shaft 820 may have an outer diameter 820a in a range of between 0.38 mm and 0.42 mm; for example, outer shaft 820 may have an outer diameter 820a of 0.40 mm. In various embodiments, and without limitation, outer shaft 820 may have an outer diameter 820a that is at least one of: 0.25 mm, 0.26 mm, 0.27 mm, 0.28 mm, 0.29 mm, 0.30 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.51 mm, 0.52 mm, 0.53 mm, 0.54 mm, 0.55 mm, 0.56 mm, 0.57 mm, 0.58 mm, 0.59 mm, 0.60 mm, or a range thereof.

As illustrated in FIG. 8, the proximal end of outer shaft 820 may have a reduced outer diameter 865a, such that the proximal end of the outer shaft may be received at least partially within the outer member 860. This arrangement may provide a smooth outer surface at the intersection 865 between the outer shaft 820 and the outer member 860, and may also improve the stability of the guide wire 800 while the outer member 860 is manipulated. In some embodiments, the outer diameter 820a of the outer shaft 820 may be reduced to outer diameter 865a at intersection 865. The reduced outer diameter 865a of the outer shaft 820 may be in a range of between 0.20 mm and 0.56 mm; for example, outer shaft 820 may have a reduced outer diameter 865a of 0.31 mm at intersection 865. In various embodiments, and without limitation, outer shaft 820 may have a reduced outer diameter 865a at intersection 865 that is at least one of: 0.20 mm, 0.21 mm, 0.22 mm, 0.23 mm, 0.24 mm, 0.25 mm, 0.26 mm, 0.27 mm, 0.28 mm, 0.29 mm, 0.30 mm, 0.31 mm, 0.32 mm, 0.33 mm, 0.34 mm, 0.35 mm, 0.36 mm, 0.37 mm, 0.38 mm, 0.39 mm, 0.40 mm, 0.41 mm, 0.42 mm, 0.43 mm, 0.44 mm, 0.45 mm, 0.46 mm, 0.47 mm, 0.48 mm, 0.49 mm, 0.50 mm, 0.51 mm, 0.52 mm, 0.53 mm, 0.54 mm, 0.55 mm, 0.56 mm, or a range thereof.

In some embodiments, the outer shaft 820 may have an inner diameter 820b in a range of between 0.10 mm and 0.40 mm; for example, outer shaft 820 may have an inner diameter 820b of 0.20 mm. In various embodiments, and without limitation, outer shaft 820 may have an inner diameter 820b that is at least one of: 0.10 mm, 0.11 mm, 0.12 mm, 0.13 mm, 0.14 mm, 0.15 mm, 0.16 mm, 0.17 mm, 0.18 mm, 0.19 mm, 0.20 mm, 0.21 mm, 0.22 mm, 0.23 mm, 0.24 mm, 0.25 mm, 0.26 mm, 0.27 mm, 0.28 mm, 0.29 mm, 0.30 mm, 0.31 mm, 0.32 mm, 0.33 mm, 0.34 mm, 0.35 mm, 0.36 mm, 0.37 mm, 0.38 mm, 0.39 mm, 0.40 mm, or a range thereof.

In use, outer member 860 may be moved axially relative to the outer shaft 820 to control the curvature of the deflectable segment (not pictured). Movement of the outer member 860 proximally may cause shortening of the length of the intersection 865 between the outer shaft 820 and the outer member 860. In some embodiments, intersection 865 may include a stopper or detent configured to prevent proximal movement of the outer member 860 beyond a certain position. Outer member 860 may also be moved distally relative to the outer shaft 820, thus increasing the length of the intersection 865. In some embodiments, outer member 860 may be moved distally until the distal end of the outer member abuts the large-diameter portion of the outer shaft 820 (e.g., the configuration illustrated in FIG. 8).

Figure 9A:
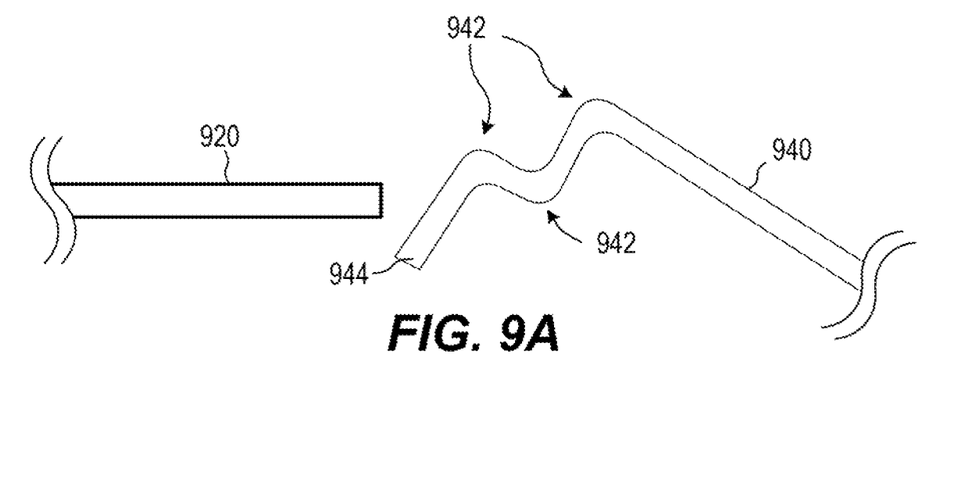
FIGS. 9A-9D illustrate an exemplary method of inserting an inner member within an outer shaft, consistent with various embodiments of the present disclosure.
Figure 9B:
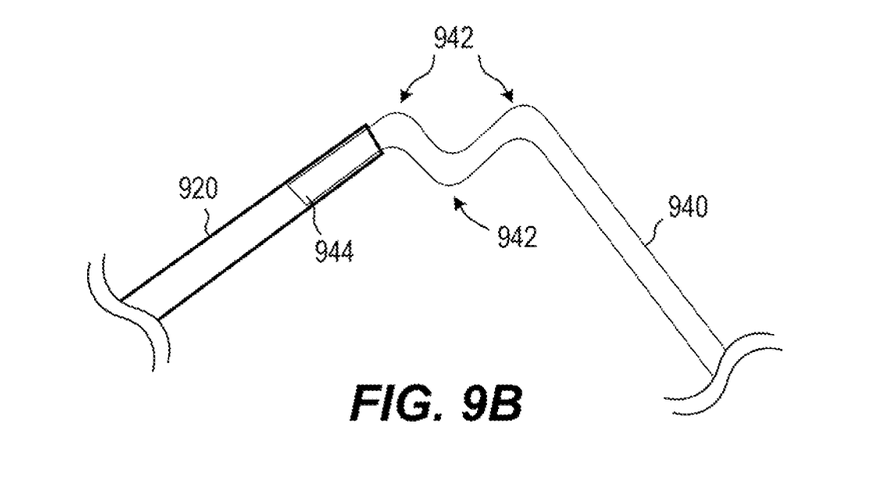
Figure 9C:
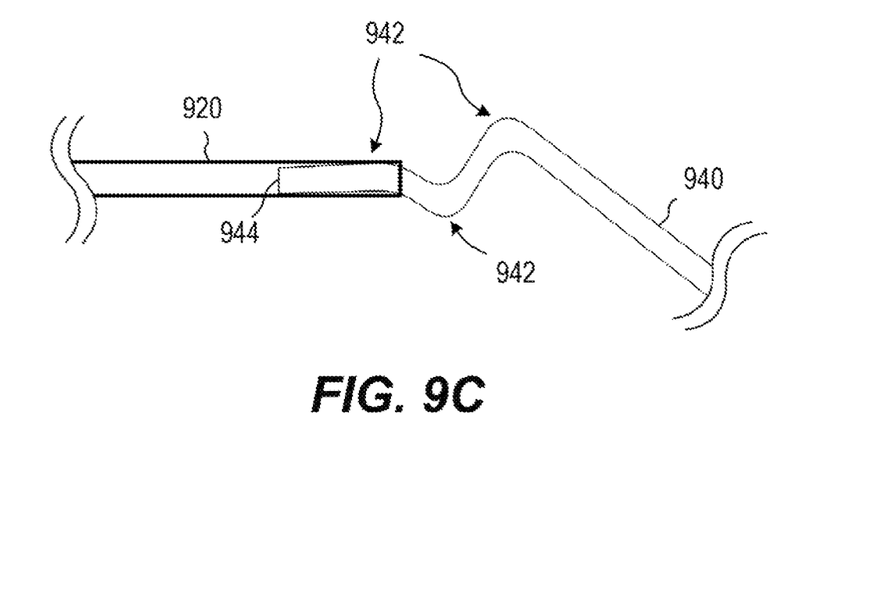
Figure 9D:
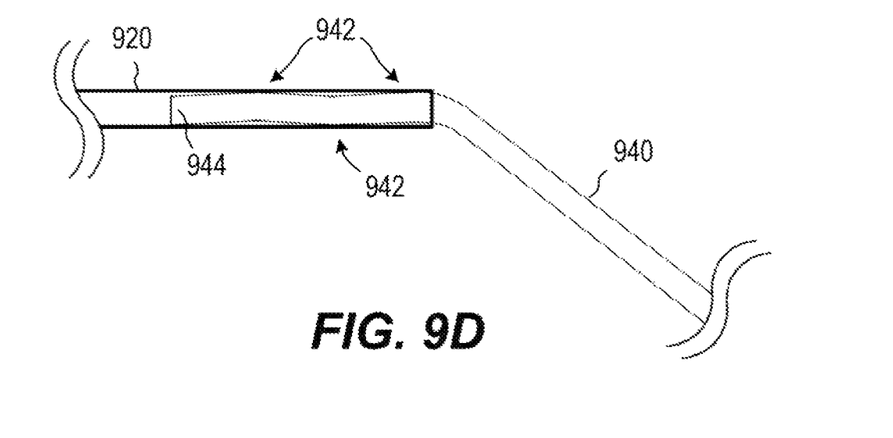

FIGS. 9A-9D illustrate an exemplary method of inserting the distal end 944 of an inner member 940 with an outer shaft 920. As illustrated in FIG. 9A, the inner member 940 may have a curved or bent configuration when situated outside of the outer shaft 920. For example, the inner member 940 may include several bends 942, causing the inner member to assume a zig-zag or serpentine configuration. The bends 942 of the inner member 940 may become partially straightened when the inner member is inserted within the outer shaft 920 (FIGS. 9B and 9C), thus achieving the friction fit therebetween. In some embodiments, the inner member 940 may be inserted distally until all of the bends 942 are situated within the outer shaft 920 (FIG. 9D).

Figure 10A:
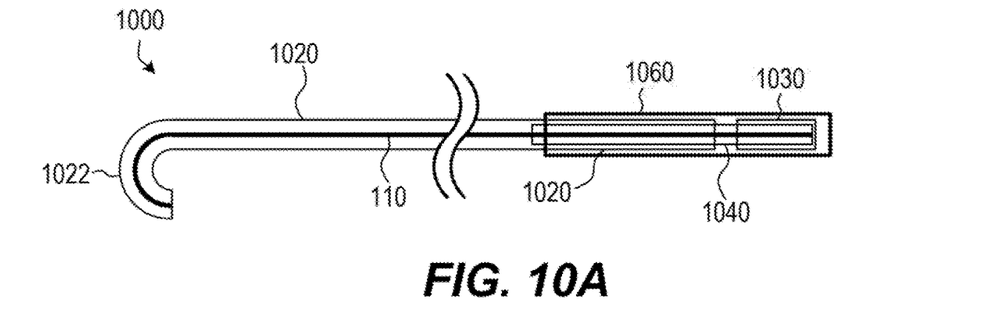
FIGS. 10A and 10B illustrate control of the distal end of an exemplary guide wire with an outer member, consistent with various embodiments of the present disclosure.
Figure 10B:
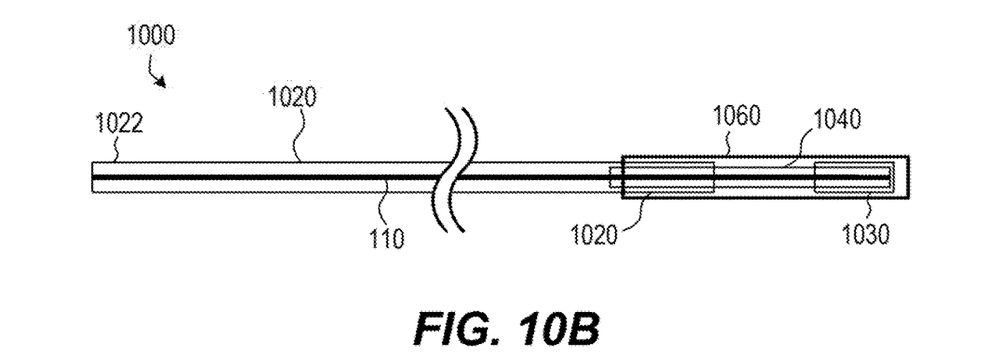
Figure 10C:
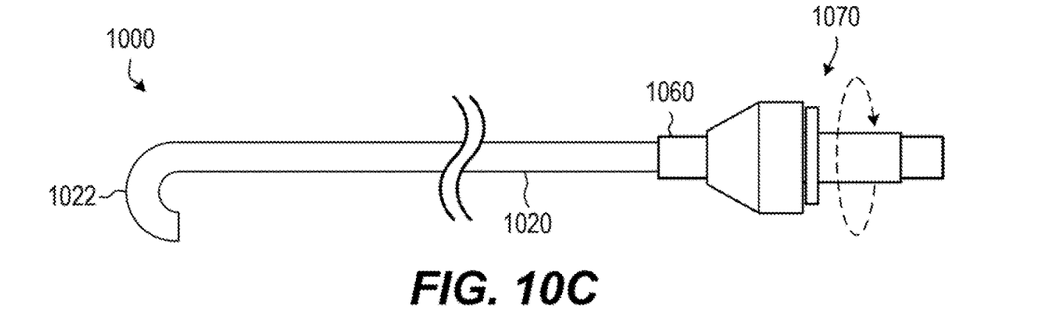
FIGS. 10C and 10D illustrate rotation of the guide wire of FIG. 10A with a torque device, consistent with various embodiments of the present disclosure.
Figure 10D:
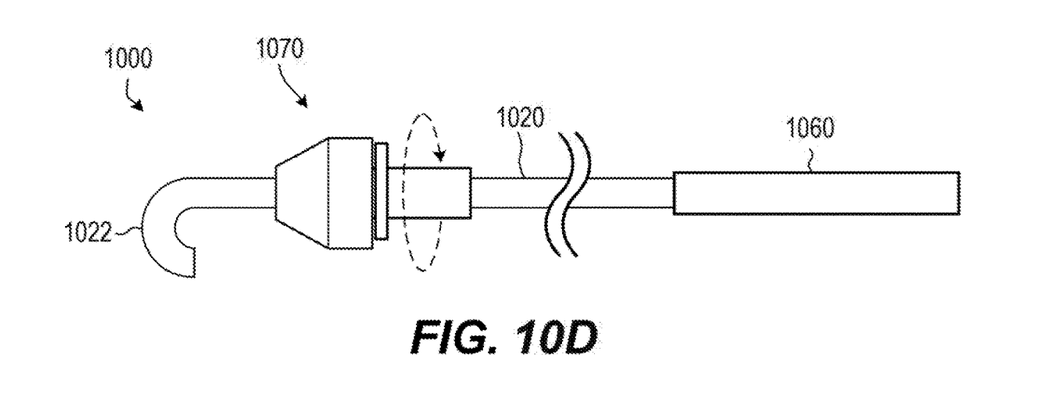

FIGS. 10A and 10B depict relative movement of the user actuation segment 1020, and optionally the outer member 1060, relative to the outer shaft 1020 to affect deflection and/or straightening of the deflectable segment 1022. The friction fit between the inner member 1040 and the outer shaft 1020 may hold the deflectable segment 1022 in the desired deflection or straightened configuration during maneuvering of the guide wire 1000. For example, FIGS. 10C and 10D illustrate deflectable segment 1022 held in a desired deflection configuration while a torquer 1070 is inserted onto and removed from the guide wire 1000. The torquer 1070 may be secured to the guide wire 1000 at any point to rotate the guide wire. For example, FIG. 10C illustrates anchoring of the torquer 1070 to the outer member 1060 and rotation of the torquer to effect rotation of the guide wire 1000. In addition, FIG. 10D illustrates anchoring of the torquer 1070 to the outer shaft 1020 and rotation of the torquer to effect rotation of the guide wire 1000. In both configurations, the friction fit between the inner member 1040 and the outer shaft 1020 may hold the deflectable segment 1022 in the desired curved or straightened configuration during rotation of the guide wire 1000 by the torquer 1070.

Figure 11:
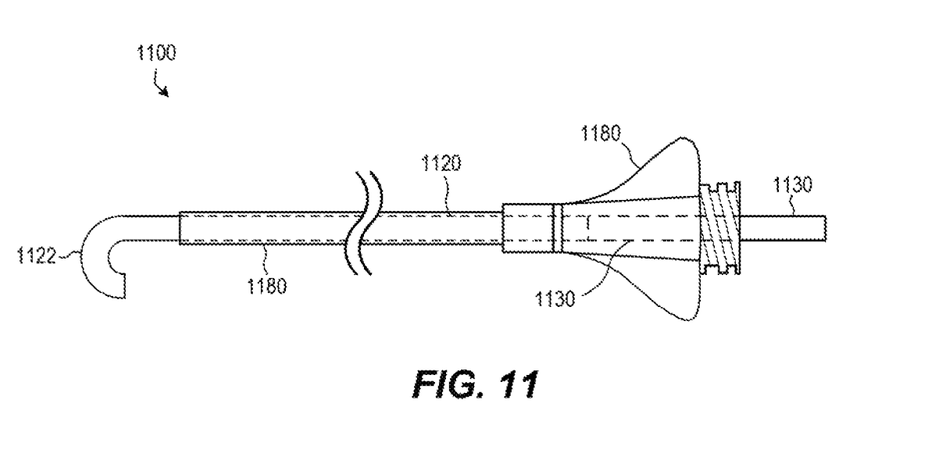
FIG. 11 illustrates advancement of a microcatheter over an exemplary guide wire, consistent with various embodiments of the present disclosure.

FIG. 11 depicts an exemplary guide wire 1100 with a microcatheter 1180 situated thereon. In FIG. 11, portions of the guide wire 1100 situated within microcatheter 1180 are depicted in broken lines. In some embodiments, the outer diameter of the user actuation segment 1130 may be substantially equal to or less than the outer diameter of the outer shaft 1120. As a result, a device such as the microcatheter 1180 may be passed over the guide wire 1100, including the user actuation segment 1130, and delivered into the body while the friction fit holds the user actuation segment 1130, and thus the deflectable segment 1122, stationary. In some embodiments, a catheter exchange maneuver may be performed with guide wire 1100 while the friction fit holds the guide wire components stationary. In a catheter exchange maneuver, a first microcatheter may be removed from the guide wire 1100 and a second microcatheter inserted over the guide wire 1100. Because the friction fit remains during the exchange maneuver, the deflectable segment 1122 retains the desired deflection configuration and the distal end of the guide wire 1100 does not become displaced during the exchange.

While illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as example only, with a true scope and spirit being indicated by the following claims and their full scope of equivalents.

What is claimed is:

1. An intraluminal guide wire, comprising:
  a hollow elongated shaft having a proximal end and a distal end, the hollow elongated shaft extending between the distal end and the proximal end;

a user actuation segment situated proximally to the proximal end of the hollow elongated shaft, wherein the user actuation segment is configured to move relative to the hollow elongated shaft;

a core wire extending between the user actuation segment and the distal end of the hollow elongated shaft; and an inner member comprising:
- a proximal end situated at least partially within, and fixed relative to, the user actuation segment, and
- a distal end configured for placement at least partially within, and for axial movement relative to, the hollow elongated shaft, wherein the core wire passes through the inner member, wherein a locking segment of the inner member configured for placement within the hollow elongated shaft is configured to exhibit a friction-based restraint on movement within the hollow elongated shaft, the friction-based restraint on movement being a frictional force between an outer surface of the inner member and an inner surface of the hollow elongated shaft, wherein the locking segment of the inner member includes at least one bend, such that when the locking segment of the inner member is inserted within the hollow elongated shaft, the at least one bend of the inner member is configured to exert the frictional force upon the inner surface of the hollow elongated shaft, and wherein an outer diameter of the inner member at the at least one bend is smaller than the diameter of the inner surface of the hollow elongated shaft.

2. The intraluminal guide wire of claim 1, wherein the hollow elongated shaft includes a deflectable segment that encompasses the distal end of the hollow elongated shaft.

3. The intraluminal guide wire of claim 1, wherein the locking segment of the inner member is sufficiently flexible such that the at least one bend is configured to be at least partially straightened when the locking segment of the inner member is inserted within the hollow elongated shaft.

4. The intraluminal guide wire of claim 1, wherein the locking segment of the inner member includes a plurality of bends, each bend of the plurality of bends being configured to exert the frictional force upon separate portions of the inner surface of the hollow elongated shaft.

5. The intraluminal guide wire of claim 1, further comprising:
- a connection member fixed relative to the user actuation segment and extending from the proximal end of the user actuation segment.

6. The intraluminal guide wire of claim 1, wherein an outer diameter of the user actuation segment is smaller than or substantially equal to an outer diameter of the hollow elongated shaft.

7. The intraluminal guide wire of claim 1, further comprising:
- an outer handle fixed relative to the user actuation segment, wherein the outer handle is configured to receive the proximal end of the hollow elongated shaft.

8. The intraluminal guide wire of claim 7, wherein at least a portion of the core wire extends within and is secured relative to the outer handle.

9. The intraluminal guide wire of claim 1, wherein the locking segment of the inner member is configured to have a helical arrangement, a zigzag arrangement, or a sinusoidal arrangement.

10. The intraluminal guide wire of claim 1, wherein the inner member is constructed from a superelastic material.

11. The intraluminal guide wire of claim 2, wherein the core wire is affixed to the deflectable segment.

12. The intraluminal guide wire of claim 2, wherein movement of the user actuation segment causes deflection of the deflectable segment.

13. The intraluminal guide wire of claim 5, wherein the connection member is connected to, or integrally formed with, the inner member.

14. The intraluminal guide wire of claim 5, wherein the connection member includes at least one bend, such that the at least one bend of the connection member is configured to exert a second frictional force upon an inner surface of a second hollow elongated shaft.

* * * * *